(12) United States Patent
Jain et al.

(10) Patent No.: US 6,909,919 B2
(45) Date of Patent: Jun. 21, 2005

(54) CARDIAC LEAD INCORPORATING STRAIN GAUGE FOR ASSESSING CARDIAC CONTRACTILITY

(75) Inventors: Mudit Jain, Woodbury, MN (US); Qingsheng Zhu, Little Canada, MN (US); Rodney W. Salo, Fridley, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 426 days.

(21) Appl. No.: 10/236,310

(22) Filed: Sep. 6, 2002

(65) Prior Publication Data

US 2004/0049255 A1 Mar. 11, 2004

(51) Int. Cl.[7] .................................................. A61N 1/05
(52) U.S. Cl. ........................................ 607/119; 600/374
(58) Field of Search .................... 607/119, 121–132; 600/547, 374–375

(56) References Cited

U.S. PATENT DOCUMENTS

| | | | | | |
|---|---|---|---|---|---|
| 2,976,865 A | * | 3/1961 | Shipley | ...................... | 600/488 |
| 4,023,562 A | * | 5/1977 | Hynecek et al. | ............ | 600/561 |
| 4,566,456 A | * | 1/1986 | Koning et al. | ................ | 607/23 |
| 4,730,619 A | * | 3/1988 | Koning et al. | ................ | 607/23 |
| 4,858,611 A | * | 8/1989 | Elliott | ......................... | 607/20 |
| 5,247,945 A | * | 9/1993 | Heinze et al. | ............. | 607/129 |
| 5,496,361 A | * | 3/1996 | Moberg et al. | ............. | 607/122 |
| 5,800,471 A | | 9/1998 | Baumann | ..................... | 607/25 |

* cited by examiner

*Primary Examiner*—Carl Layno
(74) *Attorney, Agent, or Firm*—Thomas J. Nikolai; Nikolai & Mersereau, P.A.

(57) ABSTRACT

For chronic monitoring of the effects of pacing and/or drug therapy in treating CHF, a strain gauge element is disposed at the distal end of a cardiac lead and is effective to produce a signal relating to the amount of flexure being induced into the lead by the beating action of the heart.

13 Claims, 3 Drawing Sheets

CARDIAC LEAD INCORPORATING STRAIN GAUGE FOR ASSESSING CARDIAC CONTRACTILITY

BACKGROUND OF THE INVENTION

I. Field of the Invention

This invention relates generally to cardiac rhythm management devices, and more particularly to an apparatus for determining the efficacy of pacing/defibrillation therapy chronically using a catheter mounted strain gauge placed on or in the heart.

II. Discussion of the Prior Art

It is now recognized that patients suffering from congestive heart failure (CHF) can be benefited using a cardiac rhythm management device (CRMD) to deliver cardiac stimulating pulses to the heart in timed relation to the heart's own cardiac cycle. For example, the Baumann U.S. Pat. No. 5,800,471 describes a cardiac rhythm management device especially designed for treating CHF. The device described in the Baumann '471 patent incorporates a programmed microcontroller that is operative to adjust the pacing mode and/or AV delay of the CRMD so as to achieve optimum hemodynamic performance. One measure of hemodynamic performance is the heart's contractility, which is a measure of the strength of the pumping action of the heart.

It is known in the art to provide a pressure sensor in one or more cardiac chambers to monitor pressures in the atrial and/or ventricular chambers of the heart in assessing contractility. Electrogram signals have also been signal processed and used to infer changes in contractility. More recently, a chronically implantable intracardiac acceleration sensor has been developed by Sorin Biomedica, of Saluggia, Italy, that allows quantitation of cardiac acceleration. The sensor is a micromass, uniaxial acceleration sensor located in the pacing tip of a standard unipolar pacing lead, which is adapted to be implanted in the apex of the right ventricle. Because the sensor capsule is non-deformable, the accelerometer is thought to be relatively insensitive to the potential effects of tissue encapsulation. During isometric contraction of the heart, the myocardium generates vibrations, the audible component of which comprises the first heart sound, that can be detected by intracardiac accelerometry. Because this occurs during isovolumic contraction, the effect is independent of after-load and may reflect myocardial contractility. Because the left ventricular musculature comprises most of the myocardium, the peak-to-peak amplitude of the peak endocardial acceleration has been hypothesized to reflect left ventricular contractility. Further information concerning the use of an acceleration sensor for measuring peak endocardial acceleration can be found in a paper by Occhetta et al. entitled "Experience With a New Myocardial Acceleration Sensor During Dobutamine Infusion and Exercise Test", published in the European Journal of Cardiac Pacing Electrophysiology, Vol. 5, pp. 204–209 (1995).

Generally speaking, the availability of miniature accelerometers available to measure fractional "g" range changes is low and this is based on the fact that accelerometer sensitivity is inversely proportional to the mass of the accelerometer. Thus, a need exists for an improved sensor that can be chronically placed in or on the heart for measuring contractility changes occasioned by the administration of pacing or drug therapy to patients suffering from CHF. The present invention fulfills such a need.

SUMMARY OF THE INVENTION

In accordance with the present invention, there is provided a cardiac lead that comprises an elongated, flexible, elastomeric lead body which is adapted for placement on or in the heart of a patient where the lead has a proximal end, a distal end and a plurality of electrical conductors contained within the lead body and insulated from one another. The plurality of electrodes extend from the proximal end to a zone proximate the distal end. Located in the zone near the distal end of the lead is a strain gauge element that is connected to two of the plurality of conductors. By placing the transvenous lead in either of the cardiac chambers, cardiac function or cardiac contractility, and the effects of therapy delivery thereon, can be monitored on a chronic basis. This is due to the fact that the beating action of the heart places a strain on the lead that is sensed by the strain gauge element as the lead is made to flex or bend with each heart contraction.

There are, of course, additional features of the invention that will be described hereinafter which will form the subject matter of the appended claims. Those skilled in the art will appreciate that the preferred embodiments may readily be used as a basis for designing other structures, methods and systems for carrying out the several purposes of the present invention. It is important, therefore, that the claims be regarded as including such equivalent constructions since they do not depart from the spirit and scope of the present invention. The foregoing and other features and other advantages of the invention will be apparent from the following more particular description of preferred embodiments of the invention, as illustrated in the accompanying drawings.

DESCRIPTION OF THE PREFERRED EMBODIMENT

Figure 1:
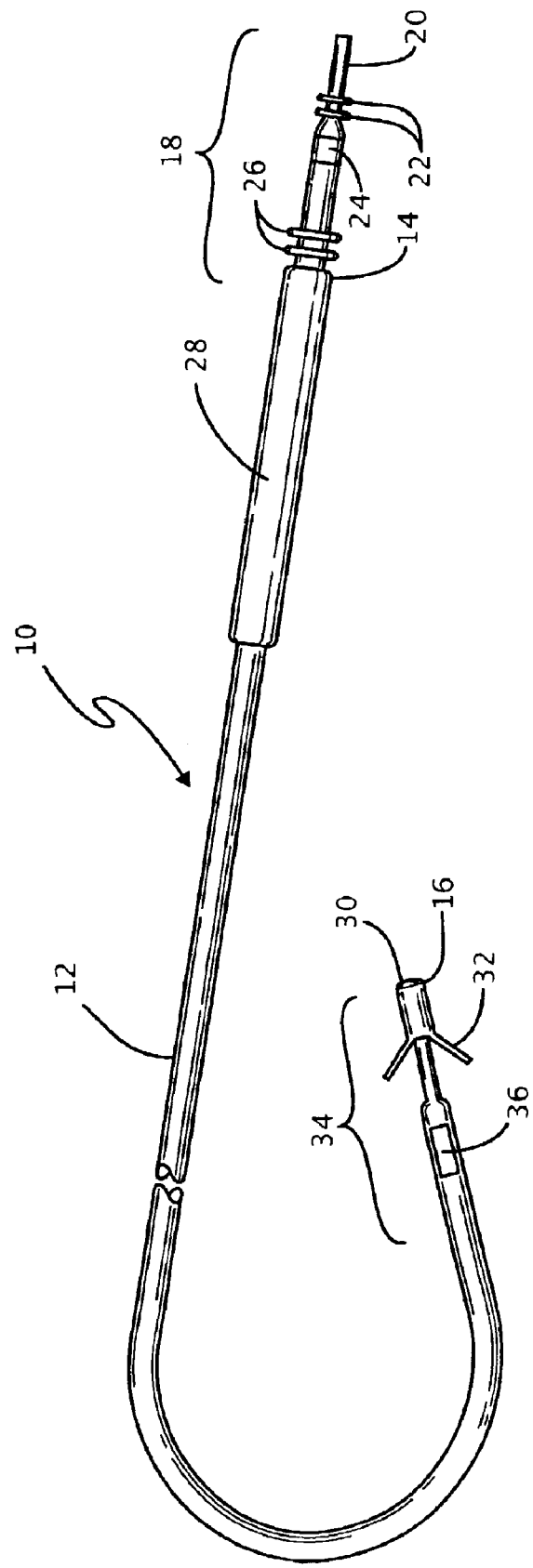
FIG. 1 is a perspective view of a cardiac lead constructed in accordance with the present invention.
Figure 2:
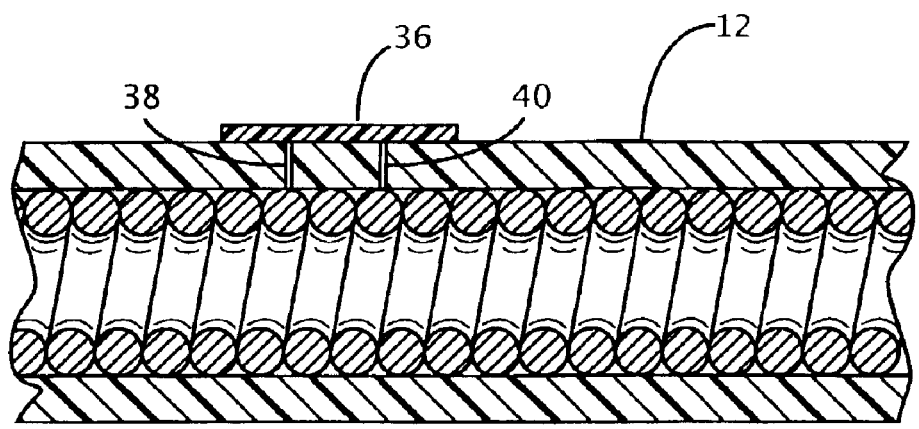
FIG. 2 is a detailed cross-sectional view of a portion of the distal end of the cardiac lead of FIG. 1.

Referring first to FIG. 1, there is indicated generally by numeral 10 a cardiac lead constructed in accordance with the present invention. It is seen to comprise an elongated, flexible, elastomeric lead body 12 of a suitable medical grade plastic material, such as silicon rubber, polyurethane, or other plastics or plastic alloys commonly used in the fabrication of such leads. The lead body 12 has a proximal end 14, a distal end 16 and embedded within the lead body and insulated from one another are a plurality of conductors that extend from the proximal end 14 to the distal end 16. As shown in FIG. 2, the conductors are helically wound and are embedded in the wall of the lead body 12.

Affixed to the proximal end 14 of the cardiac lead 10 is a connector 18 having a pin type contact 20 adapted for insertion into the connector block of a CRMD. Seal members 22 encircle the pin-contact 20 to preclude body fluids from penetrating into the connector block and possibly compromising the integrity of the desired electrical connection between the pin contact 20. A further ring contact 24 is provided on the connector 18. Likewise, additional sealing rings 26 may be provided, again to preclude body fluids from entering the connector block of the CRMD.

The lead 10 is also shown as having a strain relief member 28 surrounding a proximal end portion thereof to facilitate gripping of the lead during the implantation surgery and to reinforce the lead to inhibit flexure failure at the junction of the lead with the implanted CRMD. If the cardiac lead 10 is to deliver cardiac stimulating pulses to target tissue in the heart, it will have an electrode 30 at its distal tip and it may also include one or more ring electrodes located near the lead's distal end. It may also have tines, as at 32, to help in anchoring the distal tip electrode 30.

In accordance with the present invention, located in a zone 34 proximate the distal end 16 of the lead body is a strain gauge element 36. The strain gauge element may be disposed on the surface of the lead body 12 or, alternatively, it may be embedded beneath the surface of the lead body.

Referring again to the cross-sectional view of FIG. 2, the strain gauge element 36 has short leads 38 and 40 connecting it to predetermined ones of the helically wound conductors that extend the length of the lead and are brought out to contacts of the proximal lead connector 18. The contacts on the lead mate with contacts in the header of the CRMD, as is conventional in the art.

Figure 3:
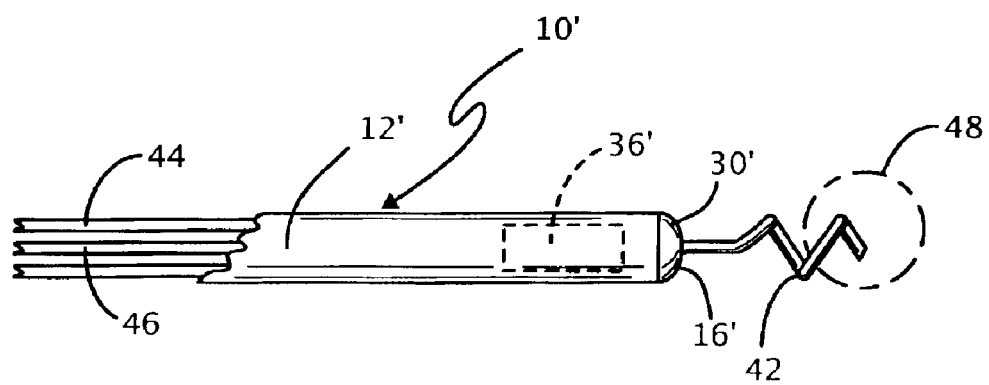
FIG. 3 is a side elevational view of an alternative embodiment of the invention.

Turning next to FIG. 3, there is shown an alternative embodiment of the present invention wherein the lead 10' has a tip electrode 30' and a positive fixation member 42 that can be advanced into cardiac tissue to hold the electrode 30' in contact with target tissue within the heart. In FIG. 3, the positive fixation device is illustrated as a rigid helix that can be advanced into tissue by rotating same. This type of lead fixation device is well known in the art. Hence, mechanisms used to advance the helical tip from within the lead body where it is shielded during transvascular implantation to an extended condition, as illustrated in FIG. 3, need not be described herein.

There is located in a zone proximate the distal end 16' a strain gauge element 36' that is depicted as being embedded in the elastomeric material comprising the lead body 12'. An electrical connection is made between the strain gauge element 36' and conductors as at 44 and 46 that run to contacts, such as 20 and 24, on the connector 18 illustrated in FIG. 1.

Figure 4:
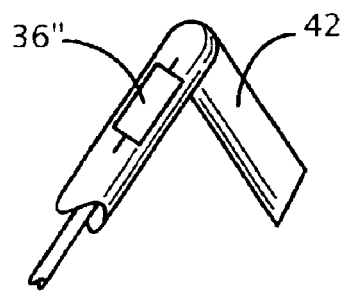
FIG. 4 is an enlarged view of the portion of the FIGURE lead of FIG. 3 shown enclosed by the broken line circle.

FIG. 4 is an enlarged portion of the helical positive fixation device 42 of FIG. 3 that is shown enclosed in the dashed line circle 48. As can be seen in FIG. 4, a strain gauge element 36" is appropriately bonded to the material comprising the positive fixation device and at a location that would be embedded within tissue such as that at the apex of the right ventricle or in the ventricular septum.

In accordance with a further feature of the present invention, multiple strain gauges may be disposed on the surface of or within the lead body at longitudinally spaced locations.

When external forces are applied to a stationary object, stress and strain are the result. Stress is defined as the object's internal resisting forces, and strain is defined as the displacement and deformation that occur. Strain may be compressive or tensile and can be measured by strain gauges, which are devices designed to convert mechanical motion into an electrical signal. A change in capacitance, inductance or resistance is proportional to the strain experienced by the sensor. The most widely used characteristic that varies in proportion to strain is electrical resistance. Although capacitance and inductance-based strain gauges have been constructed, the sensitivity to vibration of these devices, their mounting requirements, and circuit complexity needed to derive the strain-based signal, limit their application. Various forms of resistive strain gauges are also known. The metallic foil-type strain gauge consists of a grid of wire filament (a resistor) of approximately 0.001 in thickness that may be bonded directly to the strained surface by a thin layer of epoxy resin. When a load is applied to the surface, the resulting change in surface length is reflected in a resistance change, allowing the corresponding strain to be measured. While most desirable strain gauge materials tend to be sensitive to temperature variations, in the present application, the device is maintained at body temperature, which varies over only a small range that does not adversely impact the strain gauge output being measured.

A somewhat more sensitive strain gauge takes advantage of the piezoelectric or piezoresistive characteristics of germanium and silicon. Silicon wafers in which a piezoresistive element is diffused tend to be more elastic than metallic wire-type strain gauges so that after being strained, they will return more readily to their original shapes. The semiconductor bonded strain gauge measures the change in resistance with stress as opposed to strain. The wafer element usually is not provided with a backing, such that bonding it to the surface to be strained, i.e., the lead body and/or the positive fixation helix, requires some care in that only a thin layer of epoxy is used to attach it. It has the further benefit, however, of being significantly smaller in size than the metal wire strain gauge and the cost is also lower.

Another recognized disadvantage of semiconductor strain gauges is that the resistance-to-strain relationship is non-linear, and may vary as much as 10 to 20 percent from a straight-line equation. However, with computer-controlled instrumentation, software compensation can be used to overcome the non-linearity.

In applying strain gauges to the cardiac leads in accordance with the present invention, it is found desirable to place gauges on diametrically opposite surfaces of the lead body so that as the lead deforms due to the beating action of the heart, strain gauges mounted on a first surface experience tension while the strain gauge on the opposite surface experiences compression.

Figure 5:
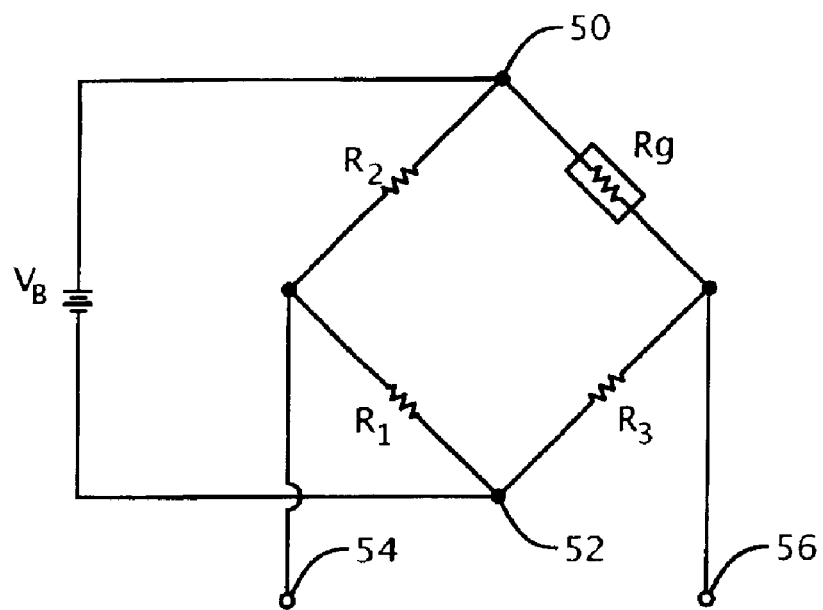
FIG. 5 is a schematic electrical drawing of a Wheatstone bridge style strain gauge sensor.

Referring now to FIG. 5, there is illustrated an electric circuit that can be integrated into the CRMD electronics and capable of measuring minute changes in resistance corresponding to the strain experienced by the strain gauge element as the lead deforms due to heart activity. The circuit of FIG. 5 is a somewhat conventional Wheatstone bridge having the strain gauge element resistance $R_g$ in one arm thereof. When a measurement is desired, the CRMD will cause a predetermined voltage $V_B$ to be applied across the terminals 50 and 52 and the resulting output voltage obtained across terminals 54 and 56 can be expressed by the formula $$V_{out} = V_B \left[ \frac{R_3}{R_3 + R_g} = \frac{R_1}{R_1 + R_2} \right].$$

The bridge is considered balanced when $R2/R1=R_g/R_3$. At this point $V_{out}$ is equal to 0. Any small change in resistance of the strain gauge will throw the bridge out of balance, making it suitable for the detection of strain.

Figure 6:
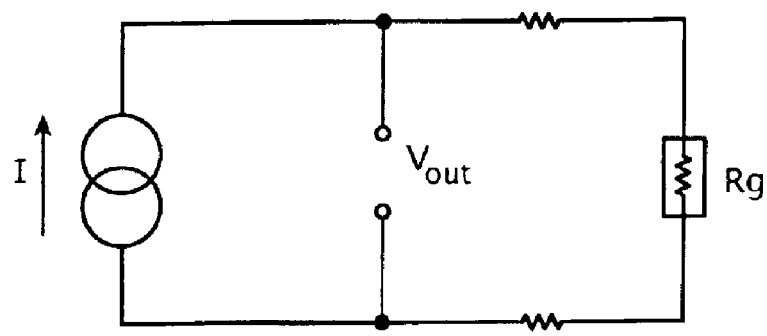
FIG. 6 is an electrical schematic drawing of a constant current strain gauge sensor.

FIG. 6 illustrates a constant current circuit that can be used to measure resistance of the strain gauge by exciting the circuit with either a constant voltage or a constant current source. In accordance with Ohms Law, if either the voltage or the current is held constant, the other will vary with the resistance. While there is no theoretical advantage to using a constant current source as compared to a constant voltage, in the present invention, the circuit output is more linear in a constant current design. Also, when a constant current source is used, it eliminates the need to sense the voltage directly at the sensor element and, therefore, only two wires need to be connected to the strain gauge element. Moreover, the constant current approach is most effective when dynamic strain is being measured as in the present application. This is because if a dynamic force is causing a change in the resistance of the strain gauge element ($R_g$), one would measure the time-varying component of the output, whereas slowly changing effects, such as changes in lead resistance due to temperature variations are rejected.

In accordance with this invention, one or more miniature strain sensors can be placed at predetermined locations on a cardiac lead and the signals derived therefrom used for monitoring and optimizing therapy. A miniature strain gauge mounted on the transvenous lead can be placed in either of the cardiac chambers to determine the cardiac function or cardiac contractility or the effective therapy delivery on the function of a particular chamber. The sensors can be either exposed to the blood or the tissue or can be enclosed inside the lead body. One or more strain gauges can be placed on the transvenous lead to be placed in the right ventricle or the coronary sinus. The bending of the lead will provide an indication of the deflection of the lead and, thus, indirectly provide information on cardiac contractility, which is an important parameter for monitoring and optimizing cardiac rhythm therapy. A right ventricular lead mounted strain gauge can also help detect tachycardia and monitor the efficacy of the therapy delivered. During tachycardia, the contractility of the cardiac chamber may be adversely affected and if cardioversion works, one can see an improvement in the cardiac contractility by noting the change in output from the strain gauge circuitry. This concept can also be extended to monitor the efficacy of pacing therapy.

This invention has been described herein in considerable detail in order to comply with the patent statutes and to provide those skilled in the art with the information needed to apply the novel principles and to construct and use such specialized components as are required. However, it is to be understood that the invention can be carried out by specifically different equipment and devices, and that various modifications, both as to the equipment and operating procedures, can be accomplished without departing from the scope of the invention itself

What is claimed is:

1. A cardiac lead comprising:
   (a) an elongated, flexible, elastomeric lead body adapted for placement on or in the heart of a patient, the lead having a proximal end and distal end and a plurality of electrical conductors contained within the lead body and insulated from one another, said plurality of conductors extending from the proximal end to a zone proximate the distal end; and
   (b) a strain gauge element disposed in said zone and connected to two of said plurality of conductors where said strain gauge element is a metallic foil element bonded to an exterior surface of the lead body.

2. A cardiac lead comprising:
   (a) an elongated, flexible, elastomeric lead body adapted for placement on or in the heart of a patient, the lead having a proximal end and distal end and a plurality of electrical conductors contained within the lead body and insulated from one another, said plurality of conductors extending from the proximal end to a zone proximate the distal end; and
   (b) a strain gauge element disposed in said zone and connected to two of said plurality of conductors where said strain gauge element is a metallic foil element embedded in the lead body.

3. A cardiac lead comprising:
   (a) an elongated, flexible, elastomeric lead body, the lead having a proximal end and distal end and a plurality of electrical conductors contained within the lead body and insulated from one another, said plurality of conductors extending from the proximal end to a zone proximate the distal end, the lead body being sized to allow transvenous placement of the zone within the coronary sinus of an animal heart; and
   (b) a strain gauge element disposed in said zone and connected to two of said plurality of conductors.

4. A cardiac lead comprising:
   (a) an elongated, flexible, elastomeric lead body having an outer diameter sized for transvascular advancement into a coronary chamber, the lead body having a proximal end, a distal end and a plurality of elongated electrical conductors encased in the lead body and extending from the proximal end to the distal end;
   (b) at least one positive fixation electrode at the distal end connected to a first of the plurality of elongated conductors;
   (c) a strain gauge element affixed to the positive fixation electrode and connected to a second and a third of the plurality of conductors; and
   (d) a connector member affixed to the proximal end of the lead body and having contacts individually connected to the first, second and third conductors, said connector adapted to be coupled to a cardiac rhythm management device.

5. The cardiac lead as in claim 4 wherein the positive fixation device is a tissue penetrating helix and the strain gauge is affixed to the helix.

6. The cardiac lead as in claim 4 wherein the positive fixation device is a tissue penetrating helix and the strain gauge is adapted to be disposed in cardiac tissue penetrated by the helix.

7. The cardiac lead of claim 4 wherein said strain gauge element is a metallic foil element bonded to an exterior surface of the lead body.

8. The cardiac lead of claim 4 wherein said strain gauge element is a metallic foil element embedded in the lead body.

9. The cardiac lead as in anyone of claims 4 or 5–8 wherein the strain gauge element forms one arm of a Wheatstone bridge circuit.

10. The cardiac lead as in any one of claim 4 wherein the strain gauge element is adapted to be intermittently connected to a constant current source in the cardiac rhythm management device by the contacts connected to the second and third conductors.

11. The cardiac lead as in any one of claims 4 or 5–8 wherein the strain gauge element produces an electrical signal output varying in relation to the heart's contractility.

12. The cardiac lead of claim 4 wherein at least a distal zone of the lead body is dimensioned for placement in the coronary sinus of an animal heart.

13. The cardiac lead as in claim 4 wherein the strain gauge element exhibits piezoelectric properties.

* * * * *